United States Patent [19]

Dinwiddie

[11] 4,103,533
[45] Aug. 1, 1978

[54] IMPACT GREASE TESTER

[75] Inventor: Curt Dinwiddie, Burbank, Calif.

[73] Assignee: Lubrication Engineers, Inc., Fort Worth, Tex.

[21] Appl. No.: 852,197

[22] Filed: Nov. 17, 1977

[51] Int. Cl.² .............................................. G01N 3/34
[52] U.S. Cl. ........................................... 73/12; 73/64
[58] Field of Search ............. 73/10, 11, 12, 64, 150 R; 35/49, 50

[56] References Cited

U.S. PATENT DOCUMENTS 2,221,731  11/1940  Biggs .................................. 73/150 X
3,859,841  1/1975  Evans et al. .............................. 73/12

*Primary Examiner*—Jerry W. Myracle
*Attorney, Agent, or Firm*—Wofford, Felsman, Fails & Zobal

[57] ABSTRACT

Apparatus for testing grease characterized by a base carrying at least two anvils for receiving grease to be tested for impact resistance, two display means surrounding the anvils for displaying any grease splattered therefrom under impact, at least two hammers carried by a pivotally mounted bracket that is freely pivotally movable so as to deliver the hammers into impact with the respective anvils and any grease thereon responsive to force, a spring for biasing the bracket and the hammers toward the anvils with a predetermined force for delivering the impact. Preferably, also, a latch is disposed on the base for holding the bracket in the predetermined angular position prior to delivering the impact when released. Also, disclosed are specific preferred embodiments and structural elements.

6 Claims, 2 Drawing Figures

IMPACT GREASE TESTER

BACKGROUND OF THE INVENTION

1. Field of the Invention

This invention relates to apparatus for testing a grease. More particularly, it relates to a device for testing the tackiness or resistance to shock loading that a grease has.

2. Description of the Prior Art

The prior art is replete with a wide variety of apparatus for testing a grease's properties; such as, viscosity, lubricity, extreme pressure lubricating properties, water resistance and tenacity. Typical apparatuses are described in the following United States patents.

U.S. Pat. No. 1,452,569 describes a side by side grease tester with objects in side by side channels being manually slidable to feel the effects of the lubricity of the respective greases.

1,990,063 describes a display device for showing the lubricating properties of greases. Rotation of a motor at low power is affected by the friction of the grease in the bearing. Centrifugal force on pivotally mounted flyweights reflect the lubricating properties.

2,700,228 demonstrates the oil viscosity with a ball in a glass tube of the oil.

3,444,629 shows a shock absorber in a side by side tester.

From the foregoing, it can be seen that the prior art has not provided a suitable test apparatus for testing the resistance of a grease to being displaced under shock loading. Expressed otherwise, the prior art has not provided apparatus for measuring the tackiness or resistance to shock loading by respective greases in side by side display apparatus.

SUMMARY OF THE INVENTION

Accordingly, it is an object of this invention to provide apparatus for testing greases to measure their relative resistance to being displaced under shock loading.

More particularly, it is an object of this invention to provide apparatus that allows simultaneously testing two greases with equal impact forces and graphically displaying the results of the test to visual observation.

These and other objects will become apparent from the following descriptive matter, particularly when taken in conjunction with the appended drawings.

In accordance with this invention, there is provided apparatus for testing grease comprising:

a. a base;
b. at least two anvil means carried by the base; each anvil means being adapted for receiving a grease sample thereon;
c. display means disposed adjacent the respective anvil means and adapted to display for visual observation any grease that is splattered from the anvil means under a predetermined impact load;
d. bracket means carried by the base and adapted to deliver respective hammer means onto the respective anvil means and any grease samples thereon with equal impact force;
e. at least two hammer means carried by the bracket means such that the hammer means are disposed one each to strike the respective anvil means and deliver an impact thereto and to any grease thereon; and
f. biasing means biasing the hammer means toward the anvil means with equal forces on each of the hammer means;

such that two greases can be emplaced on the respective anvil means and be tested for tackiness and resistance to being displaced under shock loading by equal predetermined impact forces delivered by the hammer means and the results graphically displayed on the display means.

DESCRIPTION OF PREFERRED EMBODIMENT(S)

This apparatus may be useful in testing the tackiness or resistance to being displaced undershock loading of a variety of materials. Herein, this apparatus will be described with respect to testing the resistance of a grease to being displaced under shock loading. This is a problem in many kinds of equipment, such as front end loaders or the like. Therein, the bearings that will have been greased are subjected to severe shock loading, as by trying to break hard portions of the ground with a back hoe, shovel teeth or the like. If the grease will be displaced under such shock loading, the bearings are left without adequate lubrication. Consequently, the resistance that a grease has to shock loading, sometime referred to as its "tackiness" property is important to the user. Therefore it becomes important to be able to display the respective properties of two greases for such applications if scientific and engineering evaluation is to be made.

Figure 1:
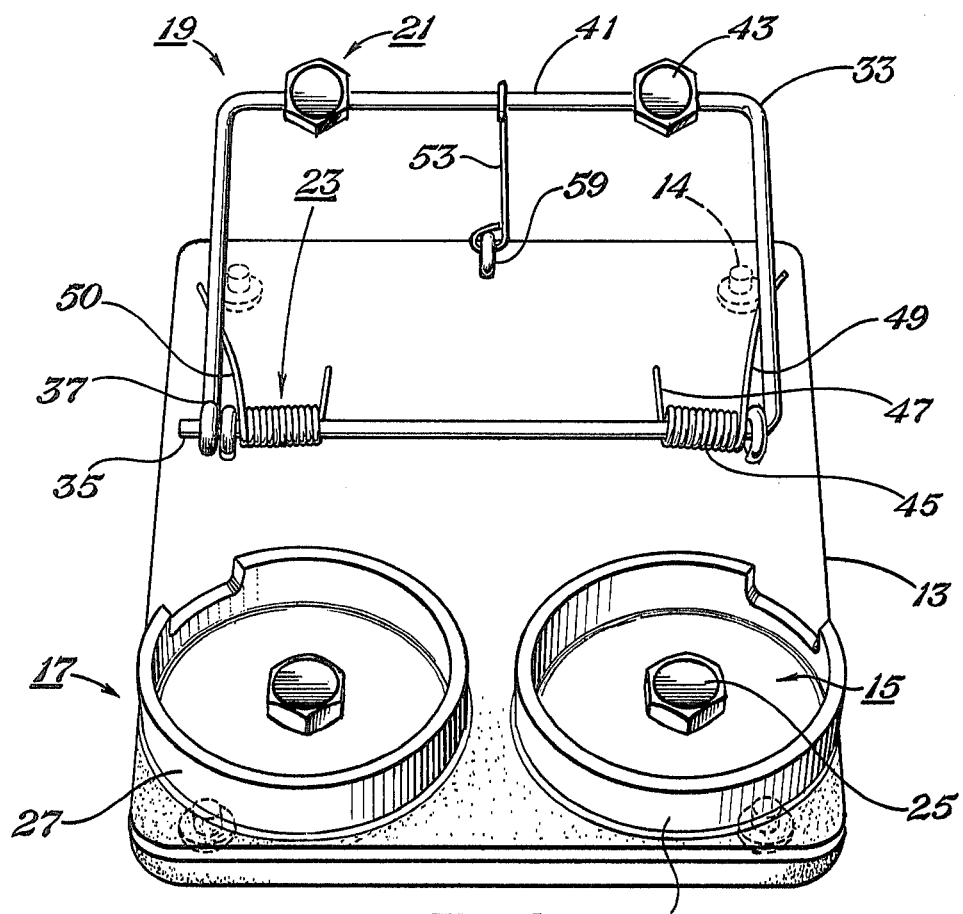
FIG. 1 is a perspective view of an embodiment of this invention ready to have the samples of grease applied to the anvil means.

Referring to the figures and, particularly, FIG. 1, the apparatus 11 includes a base 13, at least two anvil means 15, at least two display means 17, a bracket means 19, at least two hammer means 21 and a biasing means 23.

The base 13 comprises a substantially planar piece of material for readily fitting into a saleman's briefcase or the like. The base 13 carries the remaining elements of the apparatus and is adapted for sitting on a desk or other surface for demonstrating greases to a prospective customer. The base 13 may sit flat on an object. If desired, however, it may have suitable legs, or feet 14 that are affixed, as by having a shaft bonded into a well from the bottom. If desired, the feet may be screwed into the base 13. The base 13 may be formed of any material such as wood, metal, or plastic. As illustrated, it is formed of poly methyl methacrylate, commonly known as Plexiglass. Plexiglass is employed because it is readily cleaned. It can have suitable decals or the like emplaced between layers or on the back of the base and be visible through the top side. Moreover, it can be drilled or have adhered the other elements such as the anvil means.

The anvil means 15 are carried by the base 13 near one end. Each anvil means 15 is adapted for receiving a grease sample thereon. The anvil means may comprise any suitable solid object having the requisite structural strength to sustain the impact loading to be given the grease sample. As illustrated, the respective anvil means 15 comprise boltheads 25. The boltheads may be affixed by any suitable means, as by nuts on the other end and the other side of the base, by being screwed into threaded apertures or by being adhered to the base. As illustrated, a portion of the boltshaft penetrates into and is adhered to an aperture in the base 13 by epoxy, glue or the like. In any event, the anvil means serves as a solid base against which to deliver the impact force to the grease thereon. As illustrated, the boltheads 25 are formed of steel or the like, although other metallic anvil means can be employed. Moreover, the anvil means may take any suitable shape other than the illustrated hexagonal shape. For example, the anvil means may be round, square, or the like, as long as a place is provided for the grease and the anvil means serves as a solid base against which to deliver the impact force. Any grease that is splattered from the anvil means under the impact force is caught by the display means 17 for visual observation.

The display means 17 are disposed adjacent the anvil means for catching and displaying any grease splattered therefrom. As illustrated, at least two discrete pieces are disposed one each about the respective anvil means and adapted to display for visual observation any grease that splattered from the anvil means under the predetermined impact load. The illustrated display means 17 comprises a transparent means 27 for collecting and displaying any grease displaced from the anvil means under the impact load. Specifically, the transparent means 27 comprises an inverted dish with upwardly extending sides 31 that is formed of the transparent material such as poly methyl methacrylate, glass, or the like. Because of the transparency of the transparent means 27, any grease that is splattered from the respective anvil means is shown by a ring 29, FIG. 2. It is preferred to form the transparent means by injection molding or the like from a plastic such as Plexiglass that is relatively non breakable, rather than from glass which might be more friable and more easily broken. As illustrated, the respective transparent means 27 are molded with an aperture at their center to fit about the shaft of the bolt traversing from the bolthead 25 and into the base 13. Consequently, the transparent means are held in place surrounding the respective anvil means 15. The illustrated transparent means 27 are circular, although other shapes could be employed if desired. For example, they can be hexagonal, rectangular, square or even elliptical. It is preferable that they have upstanding sides 31 as well as some appreciable radial distance separating the sides 31 from the respective anvil means in order to catch the grease and provide a more dramatic display of the ring of grease that may be splattered from the respective anvil means under the impact loading delivered by the respective hammer means on the bracket means 19.

Figure 2:
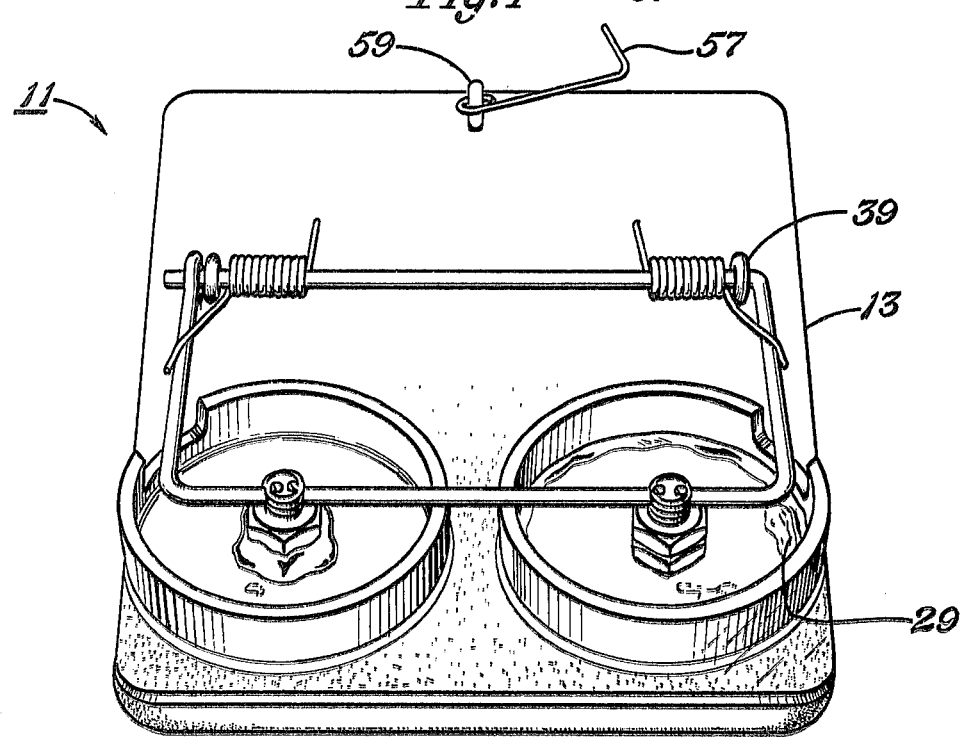
FIG. 2 is a perspective view of an embodiment of FIG. 1 after the impact loading has been delivered and showing the grease that has been splattered from one of the anvil means onto the display means.

The bracket means 19 is carried by the base 13 and adapted to deliver respective hammer means onto the respective anvil means and grease samples with equal force. The bracket means 19 is pivotally mounted on the base 13. The bracket means 19 is freely pivotally movable about a fulcrum axis responsive to respective applied torque forces. As illustrated, the bracket means 19 comprises a bail 33, that is formed in a rectangular shape with one end 35 being straight and serving as the fulcrum axis. The other end 37 is bent about the first end 35 such that the entire bail is pivotally movable. The first end 35 is mounted in suitable eyes 39 that are affixed to the base 13 and allow rotational and pivotal movement of the first end 35 and the bail 33. The eyes 39 may be affixed to the base 13 by any suitable means, such as being screwed thereinto, being bonded into suitable apertures by epoxy, glue, or the like. In the embodiment of FIGS. 1 and 2, the eyes 39 are screwed in and bonded to the base 13 so as to resist the force between the bail and the base by the biasing means. The bail 13 is formed of steel in the illustrated embodiment, although any other material such as aluminum, magnesium or the like could be employed. It is noteworthy, however, that the bracket means must be structurally adequate to stand the respective forces of the biasing means and to deliver the respective impact loading to the respective hammer means 21.

The hammer means 21 are carried by an outer radial portion 41 of the bracket means 19 such that when the outer radial portion 41 is adjacent the anvil means, the hammer means are disposed one each to strike the respective anvil means and deliver an impact thereto and to any grease thereon. The hammer means should be capable of delivering and withstanding the impact loading without deformation. As illustrated, the respective hammer means 21 comprise boltheads 43 adapted to matingly engage the boltheads 25 serving as respective anvil means. As described hereinbefore, with respect to the boltheads 25, the boltheads 43 must be formed of a material capable of withstanding the impact loading without deformation. As illustrated, they are formed of steel although other material can be employed. One advantage of employing steel boltheads is that they can be affixed by welding to the outer radial portion 41. They may be affixed by other suitable means such as thermal bonding, chemical bonding, being bolted or screwed to the outer radial portion. In any event, the respective hammer means are adapted to deliver the impact loading to the respective anvil means and any grease thereon responsive to the predetermined torque forces urged by the biasing means 23.

The biasing means 23 may comprise any means capable of imparting the force to cause the hammer means to be biased via the bracket means toward the respective anvil means with equal forces on each of the hammer means. As illustrated, the biasing means 23 comprise a pair of respective coil springs 45 for imparting the torque force to effect the accelerating pivotal movement of the bail 33 carrying the hammer means 21 in an arcuate path into impact with the grease samples on the anvil means 15. The coil springs 45 have a stabilizing member 47 that presses against the base 13. The main body of each of the coil springs 45 is disposed about the first end 35 of the bail 33. At each side, respective torque delivering members 49, 50 are disposed in an arcuate manner both the respective radial arms of the bail 33 for delivering the equal torque forces thereto and biasing the respective hammer means 21 toward the anvil means 15. Thus, a relatively large torque force is imposed against the bail 33 when it is moved back to be latched into a predetermined angular relationship with respect to the base 13, as by the latch means 53.

As illustrated, the latch means 53 comprises a metallic hook 57 for hooking over the outer radial portion 41. The hook 57 is carried in an eye 59 that is affixed to the base, similarly as described hereinbefore with respect to the eyes 39.

In operation, the apparatus is assembled as described hereinbefore. The bail 33 is pulled into its predetermined position and held by the latch means 53. Grease samples are applied respectively to the respective anvil means 15. For example, grease A may be applied to the anvil means on the left and grease B may be applied to the anvil means on the right. The quantity of grease that is applied is the same; for example, 1–5 milliliters applied as a rounded mass onto each of the anvil means.

The hook 57 is withdrawn from the outer radial portion 41 and the bail released. Under the urging of the respective biasing means 23, the bail applies equal impact loading and causes the respective hammer means to accelerate and to strike the grease on the respective anvil means. As can be seen in FIG. 2, one of the greases has remained tenaciously in contact with the anvil means so as to resist being displaced under impact loading; for example, see the grease on the left in FIG. 2. On the other hand, the grease B has been splattered from the anvil means under the impact loading and is now mostly disposed in a ring 29 on the display means 17. This illustrates dramatically the inferior "tackiness", or resistance to being displaced, possessed by grease B, on the right. Thus, the engineer who was interested in having a grease with high shock resistance would choose grease A on the left.

The advantages of this invention lie in the fact that the equal impact loading is given to the greases regardless of the point from which the bracket means 19 is released. Toward this end, the respective springs comprising the biasing means 23 are matched to insure that equal torque is given. Moreover, the metallic bail 33 is stiff enough to afford an equalizing influence even if unequal torque were delivered.

The bracket means 19 has been described as a pivotally mounted bail having an outer portion 41 that carries the hammer means in an arcuate path during acceleration toward the anvil means and grease. Any other shape bracket means can be employed, if desired. For example, respective linear tracks can be employed to direct the respective hammer means into the respective anvil means responsive to urging of the biasing means 23.

The biasing means 23, similarly, may have any form appropriate to use with the bracket means. The forms include gravity, leaf springs, compressed gas, compressed or elongated springs and torque rod, as well as the illustrated torque springs.

From the foregoing it can be seen that this invention achieves the objects delineated hereinbefore and provides apparatus for measuring the tackiness, or resistance to being displaced by shock loading, the grease may have. More particularly, it enables direct comparison to two given greases with the assurance that the equal forces will be delivered to the respective greases.

Although the invention has been described with a certain degree of particularity, it is understood that the present disclosure is made only by way of example and numerous changes in the details of construction and the combination of and arrangement of parts may be resorted to without departing from the spirit and scope of this invention.

What is claimed is:

1. Apparatus for testing grease comprising:
  a. a base;
  b. at least two anvil means carried by said base; each anvil means being adapted for receiving a grease sample thereon;
  c. display means disposed adjacent the respective said anvil means and adapted to display for visual observation any grease that is splattered from said anvil means under a predetermined impact load;
  d. bracket means carried by said base and adapted to deliver respective hammer means onto the respective anvil means and any grease thereon with equal impact forces;
  e. at least two hammer means carried by said bracket means such that said hammer means are disposed one each to strike respective said anvil means and deliver an impact thereto and to any grease thereon; and
  f. biasing means biasing said hammer means toward said anvil means with equal forces on each of said hammer means;

such that two greases can be emplaced on respective said anvil means and to be tested for tackiness and resistance to being displaced under shock loading by equal predetermined impact forces delivered by said hammer means and the results graphically displayed on said display means.

2. The apparatus of claim 1 wherein said bracket means is freely pivotally movable about a fulcrum axis responsive to respective applied torque forces and has an outer radial portion; said hammer means are carried by said outer radial portion such that when said outer radial portion can deliver respective said hammer means onto respective said anvil means; said biasing means is adapted to deliver a predetermined torque force to move said hammer means through an arc to strike said anvil means and grease samples; and said display means comprise at least two display pieces disposed one each adjacent each anvil means for displaying any grease splattered therefrom.

3. The apparatus of claim 2 wherein said apparatus includes latch means for holding said bracket means against said biasing means at a predetermined angular position with respect to said base.

4. The apparatus of claim 2 wherein said anvil means comprises boltheads, said hammer means comprises boltheads that are disposed so as to come into contact with the boltheads serving as the anvil means for delivering the impact force.

5. The apparatus of claim 2 wherein said display means comprises a transparent means surrounding each said anvil means with upwardly extending sides for receiving any grease splattered from the respective anvil means.

6. The apparatus of claim 2 wherein said bracket means comprises a metal bail pivotally mounted in brackets at each side and the biasing means comprises spring means acting on each side of said bail and against said base to apply the requisite torque force.

* * * * *